United States Patent
Gao et al.

(10) Patent No.: US 11,458,190 B2
(45) Date of Patent: Oct. 4, 2022

(54) MUSSEL ADHESIVE PROTEIN PRODUCT AND USE THEREOF FOR TREATING MUCOSAL INFLAMMATION

(71) Applicant: JIANGYIN BENGT I. SAMUELSSON INSTITUTE OF LIFE SCIENCE CO., LTD., Jiangsu (CN)

(72) Inventors: Min Gao, Jiangsu (CN); Bengt Ingemar Samuelsson, Stockholm (SE)

(73) Assignee: JIANGYIN BENGT I. SAMUELSSON INSTITUTE OF LIFE SCIENCE CO., LTD., Jiangyin (CN)

(*) Notice: Subject to any disclaimer, the term of this patent is extended or adjusted under 35 U.S.C. 154(b) by 0 days.

(21) Appl. No.: 16/589,346

(22) Filed: Oct. 1, 2019

(65) Prior Publication Data

US 2020/0101135 A1 Apr. 2, 2020

Related U.S. Application Data

(63) Continuation of application No. 15/751,551, filed as application No. PCT/CN2016/095364 on Aug. 15, 2016, now Pat. No. 10,485,848, which is a continuation-in-part of application No. PCT/CN2015/087011, filed on Aug. 14, 2015.

(51) Int. Cl.

| | | |
|---|---|---|
| C07K 2/00 | (2006.01) | |
| A61P 11/02 | (2006.01) | |
| A61K 38/17 | (2006.01) | |
| A61L 15/32 | (2006.01) | |
| A61P 35/00 | (2006.01) | |
| A61P 1/00 | (2006.01) | |
| A61P 15/00 | (2006.01) | |
| A61K 47/42 | (2017.01) | |
| A61K 9/00 | (2006.01) | |
| A61K 9/20 | (2006.01) | |
| A61K 9/06 | (2006.01) | |
| A61K 47/26 | (2006.01) | |
| A61K 47/38 | (2006.01) | |
| A61K 47/12 | (2006.01) | |
| A61K 47/02 | (2006.01) | |
| A61P 29/00 | (2006.01) | |
| A61K 35/618 | (2015.01) | |

(52) U.S. Cl.
CPC ......... *A61K 38/1767* (2013.01); *A61K 9/006* (2013.01); *A61K 9/0034* (2013.01); *A61K 9/0043* (2013.01); *A61K 9/0046* (2013.01); *A61K 9/0048* (2013.01); *A61K 9/0073* (2013.01); *A61K 9/06* (2013.01); *A61K 9/2013* (2013.01); *A61K 9/2054* (2013.01); *A61K 35/618* (2013.01); *A61K 47/02* (2013.01); *A61K 47/12* (2013.01); *A61K 47/26* (2013.01); *A61K 47/38* (2013.01); *A61K 47/42* (2013.01); *A61L 15/32* (2013.01); *A61P 1/00* (2018.01); *A61P 11/02* (2018.01); *A61P 15/00* (2018.01); *A61P 29/00* (2018.01); *A61P 35/00* (2018.01); *C07K 2/00* (2013.01)

(58) Field of Classification Search
None
See application file for complete search history.

(56) References Cited

U.S. PATENT DOCUMENTS

| | | |
|---|---|---|
| 6,395,269 B1 | 5/2002 | Fuller et al. |
| 10,485,848 B2 | 11/2019 | Gao et al. |
| 10,568,938 B2 | 2/2020 | Samuelsson et al. |
| 10,675,327 B2 | 6/2020 | Janson et al. |
| 11,090,360 B2 | 8/2021 | Janson et al. |
| 11,260,111 B2 | 3/2022 | Samuelsson et al. |
| 2002/0018787 A1 | 2/2002 | Kendall et al. |
| 2002/0168416 A1 | 11/2002 | Mitra et al. |
| 2002/0187201 A1 | 12/2002 | Bhonde et al. |
| 2003/0044470 A1 | 3/2003 | Wani et al. |
| 2005/0159396 A1 | 7/2005 | Harty |

(Continued)

FOREIGN PATENT DOCUMENTS

| | | |
|---|---|---|
| CN | 1112831 A | 12/1995 |
| CN | 101348518 A | 1/2009 |

(Continued)

OTHER PUBLICATIONS

Lee et al., "Mussel-Inspired Adhesives and Coatings," Annu. Rev. Mater. Res. 41:99-132 (2011) [Author Manuscript].
Wang et al., "Adhesion Mechanism of Mussels," Chemistry of Life 27(6):490-494 (2007).

(Continued)

*Primary Examiner* — Thomas S Heard
(74) *Attorney, Agent, or Firm* — Troutman Pepper Hamilton Sanders LLP (Rochester)

(57) ABSTRACT

The invention relates to a mussel adhesive protein (MAP) and an application thereof in inhibiting catarrh, and specifically, to applications of a MAP or a product thereof in oral mucositis, rhinitis, otitis media, pharyngitis, laryngitis, bronchitis, esophagitis, gastritis, enteritis, cervicitis, endomyometritis, inflammation resulting from inhalation injury, and oral cavity cancer, nasopharyngeal cancer, carcinoma of middle ear, conjunctival cancer, laryngeal cancer, lung cancer, esophageal cancer, stomach cancer, bowel cancer, cervical cancer, endometrial cancer, and other cancers resulting from the inflammation. The MAP can inhibit symptoms such as flush, fever, swell, and pain owing to catarrh, facilitating healing, relieving itch and pain, and having broad applications in the fields of medicines, cosmetics, medical products, disinfection products, healthcare products, foods, and household goods.

6 Claims, No Drawings

(56) References Cited

U.S. PATENT DOCUMENTS

| | | |
|---|---|---|
| 2006/0275218 A1 | 12/2006 | Tamarkin et al. |
| 2006/0275370 A1 | 12/2006 | Chung et al. |
| 2013/0052712 A1 | 2/2013 | Cha et al. |
| 2018/0221444 A1 | 8/2018 | Janson et al. |
| 2018/0228873 A1 | 8/2018 | Samuelsson et al. |
| 2018/0243371 A1 | 8/2018 | Gao et al. |
| 2020/0215166 A1 | 7/2020 | Samuelsson et al. |
| 2020/0323956 A1 | 10/2020 | Janson et al. |

FOREIGN PATENT DOCUMENTS

| | | |
|---|---|---|
| CN | 101348520 A | 1/2009 |
| CN | 101585874 A | 11/2009 |
| CN | 101991840 A | 3/2011 |
| CN | 102302417 A | 1/2012 |
| CN | 103520766 A | 1/2014 |
| CN | 104323927 A | 2/2015 |
| CN | 104645313 A | 5/2015 |
| CN | 104645320 A | 5/2015 |
| CN | 104857552 A | 8/2015 |
| EP | 2471819 A2 | 7/2012 |
| GB | 2347349 A | 9/2000 |
| KR | 20110132498 A | 12/2011 |
| RU | 2043109 C1 | 9/1995 |
| WO | 92/21354 | 12/1992 |
| WO | 99/64580 | 12/1999 |
| WO | 00/71140 A2 | 11/2000 |
| WO | 01/05411 A1 | 1/2001 |
| WO | 2013/143077 A1 | 10/2013 |
| WO | 2014/186937 A1 | 11/2014 |

Medical Device Registration Certificate of the People's Republic of China issued by the Jiangsu Food and Drug Administration on Oct. 11, 2014 (English language translation).
"What to know about enterocolitis," Medical News Today (https://www.medicalnewstoday.com/articles/318567; accessed on Jul. 10, 2021).
Couch et al., "Anti-Inflammatory Activity in Fractionated Extracts of the Green-Lipped Mussel," The New Zealand Medical Journal 95(720):803-806 (1982).
Interational Search Report and Written Opinion for International Application PCT/CN2015/084492 (dated Apr. 26, 2016).
Kim et al., "Mussel-Mimetic Protein-Based Adhesive Hydrogel," Biomacromolecules 15:1579-1585 (2014).
Nichols et al., "Skin Photoprotection by Natural Polyphenols: Anti-Inflammatory, Antioxidant and DNA Repair Mechanisms," Arch. Dermatol. Res. 302:71-83 (2010).
International Search Report and Written Opinion for International Application PCT/CN2015/084494 (dated Apr. 26, 2016).

Burzio, "Cross-Linking in Adhesive Quinoproteins: Studies with Model Decapeptides," Biochem. 39:11147-11153 (2009) (Year: 2009).
Wang et al., "Purification and Characterisation of a Novel Antioxidant Peptide Derived from Blue Mussel (*Mytilus edulis*) Protein Hydrolysate," Food Chem. 138:1713-1719 (2013).
Park et al., "Antioxidant and Anti-Inflammatory Activities of Protein Hydrolysates from Mytilus Edulis and Ultrafiltration Membrane Fractions," J. Food. Biochem. 38:460-468 (2014).
Kim et al., "Purification of a Novel Anticancer Peptide from Enzymatic Hydrolysate of Mytilus coruscus," J. Microbiol. Biotechnol. 22(10):1381-1387 (2012).
Wang et al., "Research Progress of Mussel Adhesive Proteins and its Derivatives Dopamine," Development and Application of Materials 29:101-104 (2014).
Yan et al., "Dopamine Controls Systemic Inflammation through Inhibition of NLRP3 Inflamnasone," Cell 160:62-73 (2015).
Fei et al., "Application of MAP after Treatment of Atrophic Acne Scars with Micro-Plasma," J. Clin. Dermatol. 44(1):40-42 (2015).
Kaushik et al., "Biomedical and Clinical Importance of Mussel-Inspired Polymers and Materials," Mar. Drugs 13:6792-6817 (2015).
Li et al., "Progress of Research on Pharmaceutical Values of Mussels," Fisheries Science 23(11):43-44 (2004).
Liu et al., "Cytotoxicty Tests for the Mussel Adhesive Protein Dressing for Wound Healing," Chinese Journal of Tissue Engineering Research 17(38):6785-6790 (2013).
Wang et al., "The Mechanism of Adhesion and Film Forming and their Applied Research Progress of Mussel Adhesion Proteins," J. Functional Mat. 14:14013-14020 (2014).
Zhu et al., "The Research Progress on Mussel Adhesive Proteins," Advances in Marine Science 32(4):560-570 (2014).
International Search Report and Written Opinion for corresponding Application No. PCT/CN2016/095364 (dated Oct. 8, 2016) (English translation of International Search Report only).
Gao et al., "Review on Mussel Adhesive Protein," J. Anhui Agri. Sci. 39 (32):19860-19862 (2011).
International Search Report and Written Opinion for corresponding Application No. PCT/CN2015/087011 (dated May 20, 2016) (English translation of International Search Report only).
Bandara et al., "Marine Mussel Adhesion; Biochemistry, Mechanisms, and Biomimetics," J. Adhes. Sci. and Tech. 27(18-19):2139-2162 (2012).
Gupta et al., "The Treatment of Melasma: A Review of Clinical Trials," J. Am. Acad. Dermatol. 55(6):1048-1065 (2006).
Slominski et al., "Melanin Pigmentation in Mammalian Skin and Its Hormonal Regulation," Physiol. Rev. 84(4):1155-1228 (2004).
Sklar et al., "Effects of Ultraviolet Radiation, Visible Light, and Infrared Radiation on Erythema and Pigmentation: A Review," Photochem. Photobiol. Sci. 12(1):54-64 (2013).
Rainsford and Whitehouse, "Gastroprotective and Anti-Inflammatory Properties of Green Lipped Mussel (*Pema canaliculus*) Preparation," Arzneimittelforschung 30(12):2128-32 (1980) (abstract).
Silverman and Roberto, "Understanding Marine Mussel Adhesion," Marine Biotechnology 9:661-681 (2007).
Rainsford & Whitehouse, "Gastroprotective and Anti-Inflammatory Properties of Green Lipped Mussel (Perna Canaliculus) Preparation," Drug Res. 30(II):2128-2132 (1980).

MUSSEL ADHESIVE PROTEIN PRODUCT AND USE THEREOF FOR TREATING MUCOSAL INFLAMMATION

The present application is a continuation of U.S. patent application Ser. No. 15/751,551, filed Feb. 9, 2018, which is a national stage application under 35 U.S.C. § 371 of PCT/CN2016/095364, filed Aug. 15, 2016, which claims priority of and is a continuation-in-part of PCT/CN2015/087011, filed on Aug. 14, 2015, each of which is fully incorporated by reference herein.

FIELD OF THE INVENTION

The present invention substantially relates to the technical field of drugs, cosmetics, medical products, disinfecting products, healthcare products, food, and household chemicals, and more specifically, relates to a mussel adhesive protein product and a use thereof for inhibiting mucosal inflammations.

DESCRIPTION OF THE RELATED ART

A mucous membrane is a liner of digestive, respiratory, excretory, reproductive and other organs in a body, and its surface is kept moist by mucus. Specifically, mucous membranes comprise moist liners for body cavities that open to the outside, including the oral cavity, the nasal cavity, the enteric canal, the vagina, and the intestinal tract.

Inflammation is a defensive response by an organism to irritation, with manifestations such as redness, swelling, fever, pain, and dysfunction. In an inflammatory process, on one hand, a damage factor directly or indirectly damages tissues and cells, and on the other hand, the damage factor is diluted, killed and surrounded through inflammatory hyperemia and exudation. At the same time, the damaged tissues are repaired and healed through regeneration of parenchymal and interstitial cells. Therefore, it can be stated that inflammation is a unified process of damage and anti-damage. On the other hand, inflammation has extremely complex mechanisms. Current research is mostly a fragmented elaboration of a specific mechanism of one phase or one cause thereof. To date, no internationally recognized complete theoretical system has been developed for inflammation.

Mussel adhesive protein (MAP), also known as *Mytilus edulis* foot protein (Mefp), is a special protein secreted by marine shellfish, such as *Mytilus edulis Linnaeus*, *Mytilus coruscus* and *Perna viridis*. Mussels are typically attached, in groups, to coastal reefs or ship bottom and have the ability to resist wave impacts in coastal waters. In fact, mussels can be extremely firmly attached to a base of almost any material, such as metal, wood, glass, etc. The main reason why mussels have the above characteristic is that such a special adhesive protein can be produced and stored inside the byssus gland thereof. Mussels release the adhesive protein through byssus to a surface of a solid like rock, to form a waterproof bonding and consequently fix themselves.

At present, 11 adhesive protein subtypes have been identified in mussels, including mefp-1, mefp-2, mefp-3, mefp-4, mefp-5, mefp-6, the collagens pre-COL-P, pre-COL-D, pre-COL-NQ and the mussel feet matrix proteins PTMP, and DTMP (Yaoyao Zhu, et al., Advances in Marine Science, 2014, 32(4):560-568). MAP has two structural characteristics: (1) comprising lysine, such that the protein carries a high loading of positive charge; (2) comprising 3,4-dihydroxyphenylalanine (DOPA, Levodopa). Human cells and tissues carry negative charges. MAP is tightly bonded to the cells and tissues through the static interaction between its own positive charge and the negative charge of the human cells and tissues, thereby playing a role of protection and treatment. In addition, DOPA is oxidized to produce o-diquinone, which may be crosslinked with unoxidized DOPA to form a membrane or a reticular support, such that the proteins are attached to human body surface in a tighter and firmer manner to play a protective role. MAP is a macromolecular protein, and it needs about 3-10 days to be completely degraded in the human body. It has superior ability to be attached to cells and tissues, such that MAP is stable in a local part to continuously play its role.

Despite the above characteristics of MAP, MAP products are applied in a very limited number of fields at present. Commercial MAP products include Cell-Tak by BD Biosciences from the U.S., MAP Trix by Kollodis from South Korea, and Hydrogel by Biopolymer from Sweden. These products are either directly used as a MAP solution or stored as a freeze-dried powder and dissolved prior to use. Their applications are mainly limited to micro-cellular bonding and tissue adhesive agents. There are also reports that MAP is used for fetal membrane repair, seawater corrosion-resistant coating, cardiac drug carrier, etc.

SUMMARY OF THE INVENTION

One object of the present invention is to provide MAP products.

MAP used herein refers to one or a mixture of several selected from the group consisting of 11 MAP subtypes, including mefp-1, mefp-2, mefp-3, mefp-4, mefp-5, mefp-6, the collagens pre-COL-P, pre-COL-D, pre-COL-NG, and the mussel feet matrix proteins PTMP, and DTMP, that are currently known and purified from marine mussels, such as *Mytilus edulis Linnaeus*, *Mytilus coruscus*, and *Perna viridis*, in bivalve mollusks of Mytilidae. MAP used herein may have a pH value, in an aqueous solution, in a range of pH 1.0-7.0, and in particular, in a range of pH 3.0-6.5 for better therapeutic results thereof.

MAP used herein may be obtained using the following preparation methods, for example, a method for separating and purifying MAP by using mixed adsorption chromatography according to Chinese Patent no. ZL200710179491.0, a method for purifying MAP by using carboxymethyl ion exchange chromatography according to Chinese Patent no. ZL200710179492.5, and a method for separating and purifying MAP by using salting out and dialysis according to Chinese Patent no. ZL200910087567.6.

MAP used herein may be in a form of solution or freeze-dried powder, and in particular, the MAP concentration in a product may be 0.1-15.0 mg/mL. When the concentration is overly low, MAP does not have a good effect, and when the concentration is overly high, it may cause cytotoxicity, skin irritation, etc., which is not favorable for treatment of mucosal inflammations.

MAP used herein may also be combined with excipients to prepare a liquid formulation. An exemplary MAP liquid formulation is prepared by dissolving or diluting a MAP stock solution or freeze-dried powder to a certain concentration or pH value, and the solution used for dissolution or dilution could be water, physiological saline, phosphate solution, acetate solution, borate solution, etc. MAP in the final product may have a pH value in a range of pH 1.0-7.0, and in particular, in a range of pH 3.0-6.5 for better therapeutic results thereof.

MAP used herein may also be combined with excipients to prepare a gel formulation. An exemplary MAP gel formulation is prepared by mixing a MAP solution or freeze-dried powder with a gel matrix material, and the gel matrix material may be one or any combination of cellulose derivatives, carbomer and alginates, gummi tragacanthae, gelatin, pectin, carrageenan, gellan gum, starch, xanthan gum, cationic guar gum, agar, noncellulosic polysaccharides, vinyl polymers, acrylic resins, polyvinyl alcohol and carboxyvinyl polymer.

MAP used herein may also be prepared into a foam formulation. An exemplary MAP foam formulation is made by mixing a MAP solution or freeze-dried powder with a foaming agent matrix, and said foaming agent matrix material may comprise one or any combination of hydroxypropyl methyl cellulose, gelatin, polyethylene glycol, sodium dodecyl sulfate, sodium fatty alcohol polyoxyethylene ether sulfonate, corn gluten powder and acrylamide. A particular advantage is that the foaming agent releases pressure during the defoaming process, which is more favorable for attachment, permeation and onset of MAP at an affected part. At the same time, the foaming agent has a long defoaming time, which extends the action time and makes the MAP onset more significant.

Those skilled in the art may choose the above formulations or other appropriate formulations according to characteristics of clinical indications at different stages.

All the above formulations may be prepared with methods known in the art, and reference may be made to, for example, "Pharmaceutical Preparation", for detailed operating steps.

MAP used herein may be used as a main raw material to prepare a drug along with a pharmaceutically acceptable carrier. The drug may be a liquid formulation, a gel formulation, or a foam formulation. The drug may be administered through oral administration, buccal administration (sublingual), perfusion (per rectum), drops (eye), spray (oral, nasal), inhalation (oral, nasal), spray coating (mouth, nose, ear, cervix, etc.), cavity scopes (hysteroscope, laparoscope, etc.), directional local sustained release, or targeted administration, and can be administered at low temperature or through heating.

MAP used herein may be used as a main raw material to prepare a medical device. The term used herein, medical device, refers to a material used, directly or indirectly, on human body or other similar or related objects. The medical device may be a liquid formulation, a gel formulation, or a foam formulation. The medical device may be administered through oral administration, buccal administration (sublingual), perfusion (per rectum), drops (eye), spray (oral, nasal), inhalation (oral, nasal), spray coating (mouth, nose, ear, cervix, etc.), cavity scopes (hysteroscope, laparoscope, etc.), directional local sustained release, or targeted administration, and can be administered at low temperature or through heating.

MAP used herein may be used as a main raw material to prepare a cosmetic along with excipients that are acceptable in the field of cosmetics. The cosmetic may be a liquid formulation, a gel formulation, or a foam formulation. The cosmetic may be administered through oral administration, buccal administration (sublingual), perfusion (per rectum), drops (eye), spray (oral, nasal), inhalation (oral, nasal), spray coating (mouth, nose, ear, cervix, etc.), cavity scopes (hysteroscope, laparoscope, etc.), directional local sustained release, or targeted administration, and can be administered at low temperature or through heating.

MAP used herein may be used as a main raw material to prepare a disinfecting product along with excipients that are acceptable in the field of disinfecting products. The term used herein, disinfecting product, refers to a disinfectant, a disinfecting device, a sanitary product and a disposable medical article that kills or eliminates pathogenic microorganisms in the environment in a chemical, physical or biological manner. The disinfecting product may be a liquid formulation, a gel formulation, or a foam formulation. The disinfecting product may be administered through oral administration, buccal administration (sublingual), perfusion (per rectum), drops (eye), spray (oral, nasal), inhalation (oral, nasal), spray coating (mouth, nose, ear, cervix, etc.), cavity scopes (hysteroscope, laparoscope, etc.), directional local sustained release, or targeted administration, and can be administered at low temperature or through heating.

MAP used herein may be used as a main raw material to prepare a healthcare product or food along with excipients that are acceptable in the field of healthcare products or foods. The healthcare product or food may be a liquid formulation, a gel formulation, or a foam formulation. The healthcare product or food may be administered through oral administration, buccal administration (sublingual), perfusion (per rectum), drops (eye), spray (oral, nasal), inhalation (oral, nasal), spray coating (mouth, nose, ear, cervix, etc.), cavity scopes (hysteroscope, laparoscope, etc.), directional local sustained release, or targeted administration, and can be administered at low temperature or through heating.

MAP used herein may be used as a main raw material to prepare a household chemical along with excipients that are acceptable in the field of household chemicals. The term used herein, household chemicals, refers to a chemical product for daily use, including shampoo, bath gel, etc. The household chemical may be a liquid formulation, a gel formulation, or a foam formulation. The household chemical may be administered through oral administration, buccal administration (sublingual), perfusion (per rectum), drops (eye), spray (oral, nasal), inhalation (oral, nasal), spray coating (mouth, nose, ear, cervix, etc.), cavity scopes (hysteroscope, laparoscope, etc.), directional local sustained release, or targeted administration, and can be administered at low temperature or through heating.

Another object of the present invention is to provide a use of MAP products in inhibiting mucosal inflammations.

Surprisingly, the inventors find that MAP can mitigate swelling, edema, exudation of subcutaneous tissue fluid, and mucosal lesions caused by various mucosal inflammations.

Common mucosal inflammations comprise oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

Oral mucositis is a disease that occurs to oral cavity or soft tissue with the clinical manifestation being oral mucosal diseases, which refer to damage to the mucosa inside an oral cavity and have the following specific symptoms: mouth and tongue ulceration, dry and fissured tongue, hoarse voice, dry mouth with a bitter taste, and subsequently causing oral diseases, such as oral lichen planus, stomatitis, recurrent aphthae, and cheilitis, leading to difficulties in eating and drinking, unbearable and miserable pain in the oral cavity, and moreover, if the disease is contracted, it is recurrent and worsens each time. Oral mucositis can lead to a variety of complications in body and directly affect the health, life and work of a patient. Currently, Western medicines are often administered clinically for this disease to control the symptoms. However, it is difficult to be cured completely and is listed as one of the major difficult topics of oral diseases by the medical community.

Rhinitis means inflammatory diseases of the nasal cavity, which is inflammation of the mucous membrane inside the nose caused by viruses, bacteria, allergens, various physical and chemical factors, and some systemic diseases. Major pathological changes of rhinitis include hyperemia, swelling, exudation, hyperplasia, atrophy or necrosis of the mucous membrane inside the nose.

Otitis media is an inflammatory response of the middle ear mucosa, and is an inflammatory disease that affects all or a part of the structure of the middle ear (including eustachian tubes, cavum tympani, antrum tympanicum and mastoid cells).

Conjunctivitis is a collective term of inflammatory responses that conjunctival tissues develop under actions of external and an organism's own factors. Although conjunctivitis itself does not have a severe impact on vision, it could cause damage to vision when the inflammation affects the cornea or causes complications. According to the state and course of the disease, conjunctivitis can be classified into three types: acute, sub-acute and chronic; according to the causes, it can be classified into bacterial, viral, chlamydial, fungal and allergic; according to the characteristics of pathological changes to conjunctiva, it can be classified into acute follicular conjunctivitis, chronic follicular conjunctivitis, membranous and pseudomembranous conjunctivitis. Clinical manifestations of conjunctivitis include conjunctival congestion and increased secretion.

Pharyngitis is inflammation of pharyngeal mucosa and lymphoid tissue thereof. Acute pharyngitis is often a part of upper respiratory tract infection, and is mostly caused by viral infection. Pathological changes may include acute simple pharyngitis and acute suppurative pharyngitis. Chronic pharyngitis can be divided into chronic simple pharyngitis, chronic hypertrophic pharyngitis and chronic atrophic pharyngitis.

Laryngitis is inflammation of laryngeal mucosa and submucosa tissues. Clinical characteristics include sharp cough, swollen throat, elevated body temperature and pain. According to causes and clinical progress, it can be divided into primary and secondary, acute and chronic laryngitis. Clinically, acute catarrhal laryngitis is more common, which is often accompanied by pharyngitis.

Tracheitis is inflammatory changes to tracheal mucosa and bronchial mucosa caused by infection or non-infection factors, with increased mucus secretion and lowered activity of respiratory enzymes in epithelial villi of tracheal mucosa due to the lack of negative ions, which affects the secretion function of pulmonary alveoli, and the pulmonary ventilation and exchange functions. Major clinical characteristics include chronic cough, expectoration, or being accompanied by gasp.

Esophagitis is inflammation of the esophagus, which generally refers to inflammation caused by edema and congestion due to irritation or damage to superficial or deep tissues of the esophageal mucosa. Chemical irritation comprises gastric acid, bile, alcohol, strong acids, strong bases, and drugs; physical irritation comprises hot food and beverages, foreign bodies (fishbones and the like) lodged in the esophagus, and long-term placement of a nasogastric tube. Esophagitis may also be triggered by local damage to the esophagus due to chemotherapy or radiation therapy, or by infection by tubercle *bacillus*, fungi (*candida*) or viruses due to the weakened immune system of a patient.

Gastritis refers to acute and chronic inflammations of the gastric mucosa as a result of a variety of causes, which is often accompanied by epithelial injury, mucous membrane inflammation, and epithelial regeneration. Acute simple gastritis refers to acute generalized or localized acute inflammation of the gastric mucosa caused by a variety of external and internal factors. Symptoms and signs of acute simple gastritis are not completely the same because of different causes. There are a variety of causes, including acute stress, drugs, ischemia, bile reflux and infection. Clinically, acute simple gastritis is classified into acute erosive gastritis, acute purulent gastritis, and acute corrosive gastritis. Chronic gastritis refers to various chronic inflammatory pathological changes of the gastric mucosa due to different causes, and its incidence is the highest among various gastric diseases. Common chronic gastritis includes chronic superficial gastritis, chronic erosive gastritis, and chronic atrophic gastritis. Chronic gastric intestinal metaplasia often affects the cardia and is accompanied by loss of G cells and decreased gastrin secretion. It may also affect the gastric body and be accompanied by the loss of the oxyntic gland, which leads to the decrease of gastric acid, pepsin and endogenous factors.

Enteritis refers to enteritis and colitis caused by bacteria, viruses, fungi and parasites. Clinical manifestations mainly include abdominal pain, diarrhea, watery stool, or mucopurulent bloody stool. Some patients may also have the feeling of fever, and therefore it is also referred to as infectious diarrhea. According to various durations of the disease course, enteritis is classified into two types: acute and chronic. Clinically common enteritis includes bacillary dysentery, chronic amoebic dysentery, schistosomiasis, nonspecific ulcerative colitis and regional enteritis.

Endocervicitis, also known as inflammation of the cervical canal, has pathological changes limited to the cervical mucosa and submucous tissues, the vaginal portion of the cervix appears to be very smooth, the external cervical orifice is blocked by purulent secretion, sometimes cervical mucosal hyperplasia protrudes toward the external cervical orifice, and it the cervix is visibly congestive and red. Congestion, edema, infiltration of inflammatory cells and connective tissue hyperplasia of the cervical mucosa and submucous tissues can cause cervical hypertrophy.

Endometritis means inflammatory changes to the endometrial structure caused by various reasons. The uterine cavity has very good drainage conditions and periodic endometrial denudation, which leads to very rare opportunities for inflammations to remain in the endometrium for a long period. If an acute inflammation is not thoroughly cured, however, or if there is a frequent presence of an infection source, inflammation could be recurrent. Endometritis can be classified into acute endometritis and chronic endometritis.

Inflammation caused by inhalation injury refers to mucosal burn caused by inhalation of superheated vapor, accidental drinking of boiling water, and inhalation of flame or dry and hot air by a patient with head and neck burns. Initial manifestations of the pathological changes include mucosal congestion, edema, erosion, exudation of cellulose, and formation of a white film. Mucosal edema begins at 1-2 hours and peaks at 4-8 hours after the injury, edema gradually subsides after 2-3 days, and the white film sheds to form ulcers with various depths. In serious cases, it may result in local tissue necrosis, and even esophageal or tracheal perforation.

According to one aspect, MAP according to the present invention may be used to treat oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

According to another aspect, MAP according to the present invention may be used to inhibit an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

According to one aspect of the present invention, the present invention provides a liquid formation comprising MAP for inhibiting mucosal inflammations, wherein said mucosal inflammation may comprise any one of those described above herein.

According to another aspect of the present invention, the present invention provides a gel formation comprising MAP for inhibiting mucosal inflammations, wherein said mucosal inflammation may comprise any one of those described above herein.

According to another aspect of the present invention, the present invention provides a foam formation comprising MAP for inhibiting mucosal inflammations, wherein said mucosal inflammation may comprise any one of those described above herein.

According to one aspect of the present invention, the present invention provides a method for preparing a liquid formation comprising MAP for inhibiting mucosal inflammations, wherein said mucosal inflammation may comprise any one of those described above herein.

According to one aspect of the present invention, the present invention provides a method for preparing a gel formation comprising MAP for inhibiting mucosal inflammations, wherein said mucosal inflammation may comprise any one of those described above herein.

According to one aspect of the present invention, the present invention provides a foam formation comprising MAP prepared for inhibiting mucosal inflammations, wherein said mucosal inflammation may comprise any one of those described above herein.

DETAILED DESCRIPTION OF THE PREFERRED EMBODIMENTS

Embodiments of the present invention comprise:

1. The use of MAP in the treatment of mucosal inflammations.

2. The use of MAP according to Embodiment 1, wherein the MAP is one or a mixture of several selected from the group consisting of subtypes mefp-1, mefp-2, mefp-3, mefp-4, mefp-5, mefp-6, the collagens pre-COL-P, pre-COL-D, pre-COL-NG and the mussel feet matrix proteins PTMP, and DTMP.

3. The use of MAP according to Embodiment 1, wherein the MAP concentration may be 0.1-15.0 mg/mL.

4. The use of MAP according to Embodiment 1, wherein the MAP may be a liquid formulation, a gel formulation, or a foam formulation in use.

5. The use of MAP according to Embodiment 1, wherein MAP in the final product may be in a range of pH 1.0-7.0, and in particular, in a range of pH 3.0-6.5.

6. The use of MAP according to any one of Embodiments 1-5, wherein the mucosal inflammation may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

7. The use of MAP according to any one of Embodiments 1-5, wherein the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

8. The use of MAP as an active ingredient in a composition for treatment of mucosal inflammation, wherein the composition may be a liquid formulation, a gel formulation, or a foam formulation in use.

9. The use of MAP according to Embodiment 8, wherein the composition may be administered through oral administration, buccal administration (sublingual), perfusion (per rectum), drops (eye), spray (oral, nasal), inhalation (oral, nasal), spray coating (mouth, nose, ear, cervix, etc.), cavity scopes (hysteroscope, laparoscope, etc.), directional local sustained release, or targeted administration.

10. The use of MAP according to Embodiment 8, wherein the composition may be administered at low temperature or through heating.

11. A drug for treatment of mucosal inflammations, comprising MAP and a pharmaceutically acceptable carrier, wherein the MAP concentration may be 0.1-15.0 mg/mL.

12. A medical device for treatment of mucosal inflammation, comprising MAP and a carrier acceptable in the field of medical devices, wherein the MAP concentration may be 0.1-15.0 mg/mL.

13. A cosmetic for treatment of mucosal inflammations, comprising MAP and a carrier acceptable in the field of cosmetics, wherein the MAP concentration may be 0.1-15.0 mg/mL.

14. A disinfecting product for treatment of mucosal inflammations, comprising MAP and a carrier acceptable in the field of disinfecting products, wherein the MAP concentration may be 0.1-15.0 mg/mL.

15. A healthcare product/food for treatment of mucosal inflammation, comprising MAP and a carrier acceptable in the field of healthcare products or foods, wherein the MAP concentration may be 0.1-15.0 mg/mL.

16. A household chemical for treatment of mucosal inflammations, comprising MAP and a carrier acceptable in the field of household chemicals, wherein the MAP concentration may be 0.1-15.0 mg/mL.

17. The use of MAP in a drug for treatment of mucosal inflammations, wherein the mucosal inflammation may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

18. The use of MAP in a drug for treatment of mucosal inflammations, wherein the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

19. The use of MAP in a medical device for treatment of mucosal inflammations, wherein the mucosal inflammation may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

20. The use of MAP in a medical device for treatment of mucosal inflammations, wherein the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

21. The use of MAP in a cosmetic for treatment of mucosal inflammations, wherein the mucosal inflammation may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

22. The use of MAP in a cosmetic for treatment of mucosal inflammations, wherein the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

23. The use of MAP in a disinfecting product for treatment of mucosal inflammations, wherein the mucosal inflammation may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

24. The use of MAP in a disinfecting product for treatment of mucosal inflammations, wherein the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

25. The use of MAP in a healthcare product or food for treatment of mucosal inflammations, wherein the mucosal inflammation may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

26. The use of MAP in a healthcare product or food for treatment of mucosal inflammations, wherein the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

27. The use of MAP in a household chemical for treatment of mucosal inflammations, wherein the mucosal inflammation may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

28. The use of MAP in a household chemical for treatment of mucosal inflammations, wherein the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like.

29. A gel formulation for treatment of mucosal inflammations, comprising MAP as an active ingredient.

30. A liquid formulation for treatment of mucosal inflammations, comprising MAP as an active ingredient.

31. A foam formulation for treatment of mucosal inflammations, comprising MAP as an active ingredient. In particular, the mucosal inflammation may be selected from: an oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, and the like caused by oral mucositis, rhinitis, otitis media, conjunctivitis, pharyngitis, laryngitis, tracheitis, esophagitis, gastritis, enterocolitis, cervicitis, endometritis, and the like, or may be selected from: oral mucositis, rhinitis, otitis media, conjunctivitis, pharyngitis, laryngitis, tracheitis, esophagitis, gastritis, enterocolitis, cervicitis, endometritis, an inflammation caused by inhalation injury, and the like.

32. A method for preparing a gel formulation for treatment of mucosal inflammations, which may comprise: 1) acquiring or preparing a MAP solution or freeze-dried powder, 2) acquiring or preparing a gel matrix, 3) mixing the MAP solution from Step 1) and the gel matrix from Step 2), and 4) adjusting pH to weak acidic to obtain a gel formulation.

33. A method for preparing a liquid formulation for treatment of mucosal inflammations, which may comprise: acquiring or preparing a MAP solution or freeze-dried powder, diluting with a pharmaceutically acceptable diluent, and adjusting pH to weak acidic to obtain a liquid formulation.

34. A method for preparing a foam formulation for treatment of mucosal inflammations, which may comprise: acquiring or preparing a MAP solution or freeze-dried powder, mixing with a pharmaceutically acceptable foaming agent matrix, and adjusting pH to weak acidic to obtain a foam formulation.

The present invention will be further described below with reference to specific embodiments. It should be noted that, when a drug, medical device, cosmetic, disinfecting product, healthcare product or food, or household chemical formed from MAP or various formulations of MAP according to the present invention is applied on a subject, it can be used on the indications described above and exhibits the functions described above. All formulations within the scope of the present invention have been tested, and only a small portion thereof is described below in the embodiments for the purpose of description; however, they shall not be construed as limitations to the present invention.

Unless otherwise specifically described, all reagents used in the present invention are commercially available on the market.

Example 1: Use of MAP Liquid Medical Device in Treatment of Recurrent Aphthous Ulcers Take 1 mL of a MAP solution with concentration at 10.0 mg/mL, add 9 mL of 0.1% citric acid solution, and prepare a MAP aqueous solution medical device with concentration at 1.0 mg/mL. Gather 20 patients with minor recurrent aphthous ulcer as confirmed by experts in oral mucosa for testing. The selected patients have more than 5 ulcers with no limit on positions of the ulcers. The largest ulcer is selected as a target ulcer for observation. The target ulcer has a diameter smaller than 1 cm.

The selected patients are randomly divided into a control group and a test group. The control group is treated with 0.1% citric acid solution, and the test group is treated with the above MAP medical device. For both groups, the usage is 3 times per day, spraying onto the affected parts after meals, and 2 to 3 instances of spraying for each part until the affected part is completely covered by 0.1% citric acid solution or the MAP aqueous solution medical device. In the group sprayed with the MAP aqueous solution medical device, the pain at the affected part is significantly reduced within 5 to 15 min, the visual analogue score VAS goes from 5.0-7.0 prior to the treatment down to 1.0-3.0, and the duration of pain relief can last 2 to 7 h. For the control group, the VAS score does not change for the pain at the affected part before and after the spraying. As the use time is extended, the pain relief duration is extended, and the use interval is extended, which does not show any dependence.

After 5 days of continuous spraying, all ulcers of 6 patients in the test group are cured, and 1 patient in the control group has the ulcers cured. After 7 days of continuous spraying, all patients in the test group are cured, and 3 patients in the control group are cured (see Table 1).

TABLE 1

| Observation indexes | Control group | Test group |
| --- | --- | --- |
| Average onset time (min) | — | 8.1 ± 1.2 |
| Average VAS prior to use | 5.6 ± 1.0 | 5.9 ± 0.9 |
| Average VAS after use | 5.0 ± 0.8 | 1.7 ± 0.6 |
| Average pain relief duration (h) | — | 5.2 ± 1.1 |
| Average healing time (d) | 10.5 ± 1.9 | 5.9 ± 1.2 |

Example 2: Use of MAP Gel Medical Device in Treatment of Recurrent Aphthous Ulcers Take 10 g hydroxypropylmethyl cellulose, add 20 mL deionized water, place in a bath at 90° C. for 30 min until complete dissolution to obtain a gel matrix, separately take 2.5 mL of a MAP solution with concentration at 10.0 mg/mL, add it into the gel matrix while stirring, and mix homogeneously to form a MAP gel medical device, wherein the MAP concentration is 1.0 mg/mL.

Gather 20 patients with minor recurrent aphthous ulcer as confirmed by experts in oral mucosa for testing. The selected patients have more than 5 ulcers with no limit on positions of the ulcers. The largest ulcer is selected as a target ulcer for observation. The target ulcer has a diameter smaller than 1 cm.

The selected patients are randomly divided into a control group and a test group. The control group is treated with the blank gel matrix that does not contain MAP, and the test group is treated with the MAP gel medical device. For both groups, the usage is 3 times per day, spraying onto the affected parts after meals, and 2 to 3 instances of spraying for each part until the affected part is completely covered by the blank gel or the MAP gel medical device. In the group sprayed with the MAP gel medical device, the pain at the affected part is significantly reduced within 5 to 13 min, the visual analogue score VAS goes from 5.0-7.0 prior to the treatment down to 1.0-3.0, and the duration of pain relief can last 2 to 9 h. For the control group, the VAS score does not change for the pain at the affected part before and after the spraying. As the use time is extended, the pain relief duration is extended, and the use interval is extended, which does not show any dependence.

After 5 days of continuous spraying, all ulcers of 7 patients in the test group are cured, and 3 patients in the control group have the ulcers cured. After 7 days of continuous spraying, all patients in the test group are cured, and 5 patients in the control group are cured (see Table 2).

TABLE 2

| Observation indexes | Control group | Test group |
| --- | --- | --- |
| Average onset time (min) | — | 7.6 ± 1.0 |
| Average VAS prior to use | 5.3 ± 1.4 | 5.8 ± 0.9 |
| Average VAS after use | 5.0 ± 1.1 | 1.3 ± 0.7 |
| Average pain relief duration (h) | — | 7.3 ± 1.8 |
| Average healing time (d) | 8.0 ± 1.6 | 4.7 ± 1.6 |

Example 3: Use of MAP Liquid Household Chemical in Treatment of Rhinitis

Take a MAP solution with concentration at 0.5 mg/mL, use 0.001% acetic acid to dilute by 5 times to a MAP content of 0.1 mg/mL, and obtain a MAP liquid household chemical.

Gather 10 patients with rhinitis as confirmed by otolaryngology experts, and then have them join the groups for testing. The patients have stuffy and running noses, and the nasal discharge is viscous or mucopurulent. The patients use the MAP liquid household chemical to wash the nasal cavity every day, once in the morning and in the evening, respectively. After 5 days of using the MAP liquid household chemical, all 10 patients have the stuffiness mitigated to various degrees. After 10 days of the use, all patients have the stuffiness mitigated, and no tested patients have mucopurulent or viscous nasal discharge. It proves that the MAP liquid household chemical according to the present invention can be used for treatment of rhinitis.

Example 4: Use of MAP Liquid Drug in Treatment of Rhinitis

Take a MAP solution with concentration at 2.0 mg/mL, use 0.05% citric acid to dilute by 10 times to a MAP content of 0.2 mg/mL, and obtain a MAP liquid drug.

Gather 10 patients with rhinitis as confirmed by otolaryngology experts, and then have them join the groups for testing. The patients have stuffy and running noses, and the nasal discharge is viscous or mucopurulent. The MAP liquid drug is administered to the patients every day in a manner of aerosol inhalation, once per day. After 3 days of using the MAP liquid drug, all 10 patients have the stuffiness mitigated to various degrees. After 7 days of the use, all patients have the stuffiness mitigated, and no tested patients have mucopurulent or viscous nasal discharge. It proves that the MAP liquid drug according to the present invention can be used for treatment of rhinitis.

Example 5: Use of MAP Gel Disinfecting Product in Treatment of Otitis Media

Take a MAP solution, mix with guar gum and propanetriol at a volumetric ratio of 2:1:1, add water for injection, use citric acid to adjust to pH 3.0, and prepare a MAP gel disinfecting product with the MAP content at 1.5 mg/mL.

Gather 10 patients with acute suppurative otitis media as confirmed by otolaryngology experts, and then have them join the groups for testing. The patients have earaches and pus flowing out of the ears. The patients are administered the MAP gel disinfecting product every day 3 times per day. After 3 days of using the MAP gel disinfecting product, all 10 patients no longer have the symptom of earache, and the pus in ears is decreased. After 7 days of use, no patients have pus flowing out of the ears. It proves that the MAP gel disinfecting product according to the present invention can be used in treatment of otitis media.

Example 6: Use of MAP Liquid Drug in Treatment of Otitis Media

Take a MAP solution with concentration at 5 mg/mL, add 0.001% acetic acid in an equal volume to dilute to 2.5 mg/mL, the pH of the solution is 3.0, and form a MAP liquid drug with a MAP content of 2.5 mg/mL.

Gather 10 patients with acute suppurative otitis media as confirmed by otolaryngology experts, and then have them join the groups for testing. The patients have earaches and pus flowing out of the ears. The patients are administered the MAP liquid drug every day 3 times per day. After 3 days of using the MAP liquid drug, all 10 patients no longer have the symptom of earache, and the pus in the ears is decreased. After 7 days of use, no patients have pus flowing out of the ears. It proves that the liquid drug according to the present invention can be used for treatment of otitis media.

Example 7: Use of MAP Liquid Medical Device in Treatment of Conjunctivitis

Take a MAP solution, dilute with physiological saline, use acetic acid to adjust to pH 6.0, and obtain a MAP liquid medical device, wherein the MAP concentration is 3 mg/mL.

Select 15 patients with conjunctivitis, who have manifestations of conjunctival congestion, watery secretion, and irritating sensation in the eyes. They are confirmed by ophthalmologists and then join the groups for testing. Drop the MAP liquid medical device above at the affected part of the eyes 4 times per day. After sprayed with the MAP liquid medical device, the irritating sensation is weakened at the affected part within 30 min, and the duration of weakened irritation can last for 2 to 5 h on the 1st day of use of the device. After 5 days of continuous spraying, the irritating sensation is gone, conjunctival congestion is mitigated, and the secretion is decreased. After 7 days of continuous spraying of the MAP liquid medical device above, the irritation and conjunctival congestion disappear for all patients, and the secretion becomes normal. It proves that the MAP liquid medical device according to the present invention can be used for treatment of conjunctivitis.

Example 8: Use of MAP Hydrogel Healthcare Product in Treatment of Pharyngitis Take a MAP solution, mix with guar gum and propanetriol at a mass ratio of 2:1:1, dilute with physiological saline, use acetic acid to adjust to pH 5.0, and obtain a MAP hydrogel healthcare product, wherein the MAP concentration is 2.0 mg/mL.

Select 16 patients with acute pharyngitis, who have manifestations of dry throat, itching, minor pain, burning sensation and foreign object sensation, and then throat pain, most of which are burning pains, and accompanied by mucosal hyperemia. They are confirmed by otolaryngologists, and then join the groups. Spray the MAP hydrogel healthcare product above at the affected part 3 times per day after meals. After spraying with the MAP hydrogel healthcare product, the pain or itching at the affected part is reduced within 8 to 20 min, and the duration of pain relief can last 3.5 to 4.0 h. After 5 days of continuous use, the feeling of pain at throat is gone, and the throat returns to normal conditions from mucosal hyperemia. It proves that the MAP hydrogel healthcare product according to the present invention can be used for treatment of pharyngitis.

Example 9: Use of MAP Gel Drug in Treatment of Laryngitis

Take a MAP solution, mix with hydroxypropylmethyl cellulose and propanetriol at a mass ratio of 3:2:1, use citric acid to adjust to pH 6.2, and obtain a MAP gel drug, wherein the MAP concentration is 3 mg/mL.

Select 10 patients with acute laryngitis, who have manifestations of dry throat, itching, pricking sensation, burning sensation and foreign object sensation. They are confirmed by otolaryngologists, and then join the groups. Spray the MAP gel drug above at the affected part 3 times per day after meals. After spraying with the MAP gel drug, the itching or pain at the affected part is reduced within 7 to 16 min, and the duration of pain relief can last 3.0 to 4.0 h. After 5 days of continuous use, the feeling of pain, burning sensation and foreign object sensation at throat are all gone. It proves that the MAP drug according to the present invention can be used for treatment of laryngitis.

Example 10: Use of MAP Liquid Healthcare Product in Treatment of Tracheitis

Take a MAP solution, mix with propanediol at a volumetric ratio of 2:1, use acetic acid to adjust to pH 5.0, and obtain a MAP liquid healthcare product, wherein the MAP concentration is 3.0 mg/mL.

Gather 12 patients with tracheitis, whose clinical manifestations include cough, expectoration, accompanied by shortness of breath. The patients must be confirmed by respiratory physicians before they can join the groups for testing. The patients are treated via aerosol inhalation, once per day and 30 min each time. After 3 days of use, the patients have mitigated cough and a reduced amount of expectoration. After 7 days of use, no patients have expectoration, and 1 patient still has a slight cough. It proves that the MAP liquid healthcare product according to the present invention can be used for treatment of tracheitis.

Example 11: Use of MAP Liquid Drug in Treatment of Esophagitis

Take a MAP solution, dilute with a borate aqueous solution to obtain a MAP liquid formulation, with pH of 5.5, wherein the MAP concentration is 2.5 mg/mL.

Gather 20 patients with esophagitis for testing. Per esophagoscopy, the patients have the following manifestations: congestion, edema, surface erosion and small and superficial ulcers of esophageal mucosa, and the patients are confirmed by doctors in digestive internal medicine and then join the groups. The drug is administered to the patients via an esophagoscope, 2 times per day and 3 mL each time. On the 3rd day of treatment, the scores of esophageal surface ulcer exudation and congestion both decrease from 3 in the beginning to 2 (see Table 3 for the scoring criteria). On the 7th day of treatment, the scores of esophageal surface ulcer exudation and congestion decrease to 1. On the 10th day of treatment, the scores of esophageal surface ulcer exudation and congestion decrease to 0. It proves that the MAP liquid drug according to the present invention can be used for treatment of esophagitis.

TABLE 3

| Observations | Evaluation criteria |
| --- | --- |
| Ulcer exudation | 0: None |
| | 1: Slightly wet ulcer surface |
| | 2: Small amount of gray (yellow) exudation on the ulcer surface |
| | 3: A lot of exudation and pseudomembrane on the ulcer surface |
| Ulcer congestion | 0: None |
| | 1: Slightly red |
| | 2: Cardinal |
| | 3: Purple red |

Example 12: Use of MAP Hydrogel Drug in Treatment of Gastritis

Take a MAP solution, add carboxymethyl cellulose and glycerin at a volumetric ratio of 2:1:1, and obtain a MAP hydrogel drug, wherein the MAP concentration is 2.5 mg/mL. Furthermore, wrap the MAP hydrogel drug in a gastrically soluble coating material to form a gastrically soluble sustained-release formulation.

Gather 20 gastritis patients for testing, the patients having been diagnosed and confirmed by doctors in digestive internal medicine using gastroscopy before they join the groups. The selected patients take the gastrically soluble sustained-release formulation that contains the MAP hydrogel drug through oral administration once per day and 1 tablet each time. After 3 days of treatment, perform gastroscopy on the subjects, and the subjects have their gastric ulcer surfaces healed to various degrees. After 5 days of treatment, perform gastroscopy on the subjects, and the subjects have all gastric ulcer surfaces healed.

Example 13: Use of MAP Liquid Drug in Treatment of Acute Enteritis

Take MAP freeze-dried powder, use physiological saline to prepare a 1.0 mg/mL aqueous solution, use acetic acid to adjust pH to 5.8, and obtain a MAP liquid drug. Furthermore, wrap the MAP liquid drug in an enteric coating material to form an enteric sustained-release formulation.

Gather 10 patients with acute enteritis, who have clinical manifestations of nausea, vomiting, and diarrhea, the patients having been diagnosed and confirmed by doctors in digestive internal medicine to have acute enteritis using enteroscopy before they join the study. The selected patients are treated with the enteric sustained-release formulation that contains MAP through oral administration once per day and 1 tablet each time. After 2 days of treatment, nausea, vomiting, and diarrhea are all mitigated in the patients, proving that the MAP liquid drug can be used for treatment of acute enteritis.

Example 14: Use of MAP Gel Disinfecting Product in Treatment of Cervicitis

Take a MAP solution, mix with propanetriol at a volumetric ratio of 1:1, use acetic acid to adjust to pH 4.8, and obtain a MAP gel disinfecting product.

Gather 12 patients with cervicitis, whose clinical manifestations include increased vaginal discharge, purulent mucus, and the irritation by the discharge could cause itching and burning sensation in the vulvar area. The patients are confirmed by gynecologists and then join the groups for testing. The selected patients are sprayed with the MAP gel disinfecting product every day 2 times per day. After 1 week of treatment, the discharge of the patients becomes normal, there is no itching or other feelings of discomfort, proving that the MAP gel disinfecting product according to the present invention can be used for treatment of cervicitis.

Example 15: Use of MAP Gel Medical Device in Treatment of Cervicitis

Mix a MAP solution with gelatin and alginates at a mass ratio of 4:1:1, use acetic acid to adjust to pH 4.8 to obtain a MAP gel healthcare product, wherein the MAP concentration is 5.0 mg/mL.

Gather 10 patients with cervicitis, whose clinical manifestations include increased vaginal discharge, purulent mucus, and the irritation by the discharge could cause itching and burning sensation in the vulvar area. The patients are confirmed by gynecologists and then join the groups for testing. For the selected patients, use 0.1% potassium permanganate solution to wash the vagina first, and then spray the MAP gel healthcare product on the cervical area every day once per day. After 1 week of treatment, perform a pap smear on the patients, 7 patients have normal cells at the cervical area, and 3 patients still have a small amount of inflammatory cells according to the test. After 10 days of treatment, the pap smear is normal for all the patients, the discharge becomes normal, there is no itching or other feelings of discomfort, indicating that the MAP product according to the present invention can be used for treatment of cervicitis.

Example 16: Use of MAP Foam Medical Device in Treatment of Cervicitis

Mix a MAP solution with hydroxypropyl methyl cellulose at a mass ratio of 4:1, use acetic acid to adjust to pH 4.8 to obtain a MAP foam healthcare product, wherein the MAP concentration is 5 mg/mL.

Gather 10 patients with cervicitis, whose clinical manifestations include increased vaginal discharge, purulent mucus, and the irritation by the discharge could cause itching and burning sensation in the vulvar area. The patients are confirmed by gynecologists and then join the groups for testing. For the selected patients, use 0.1% potassium permanganate solution to wash the vagina first, and then spray the MAP foam healthcare product on the cervical area every day once per day. After 1 week of treatment, perform a pap smear on the patients, all patients have normal cells at the cervical area, the discharge of the patients becomes normal, and there is no itching or other feelings of discomfort. It indicates that the MAP product according to the present invention can be used for treatment of cervicitis, and the effect is better when it is used as a foam formulation.

Example 17: Use of MAP Liquid Drug in Treatment of Endometritis

Take a MAP solution, use 0.1% citric acid to dilute to 3 mg/mL, the solution pH is 6.5 after dilution, and obtain a MAP liquid drug.

Gather 15 patients with endometritis, whose clinical manifestations include pain in the pelvic region and increased white vaginal discharge. The patients are confirmed by gynecologists to have endometritis and then join the groups for testing. Perform intrauterine administration of the above MAP liquid drug, and prior to the operation, first perform bimanual examination to determine the size and position of uterus, sterilize the vulva and vagina, detect the depth of the uterine cavity, and then send a sterilized urinary catheter into the uterine cavity via the uterine neck for 0.5 cm less than the depth of uterine cavity, slowly inject the selected drug into the uterine cavity via the urinary catheter, and when the drug liquid completely enters the uterine cavity, pull out the urinary catheter. Rest in the supine position or with hip raised for 1 to 2 h, once per day. After 10 days of use, the tested patients do not have pain in the pelvic region, and the white vaginal discharge is normal, proving that the MAP product according to the present invention can be used for treatment of endometritis.

Example 18: Use of MAP Liquid Drug in Treatment of Inhalation Injuries

Take a MAP solution with concentration at 10.0 mg/mL, use acetic acid to dilute by 2 times to a MAP concentration of 5.0 mg/mL, the solution pH is 6.8, and obtain a MAP liquid drug.

Gather 10 patients with inhalation injuries caused by inhalation of high temperature vapor, flame or dry and hot air, whose clinical manifestations include mucosal congestion, edema, erosion, exudation of cellulose, and formation of a white film. They are confirmed by otolaryngologists, and then join the groups for testing, who are treated with the above MAP liquid drug. The drug is administered via aerosol inhalation, once per day and 30 min each time. At the 2nd day of treatment, the edema caused by inhalation injuries begins to subside, and the film sheds to form ulcers. At the 8th day of treatment, all patients have the ulcers healed with the average healing time at 6.9±1.2 days. It proves that the MAP liquid drug according to the present invention can be used for treatment of inhalation injuries.

Example 19: Use of MAP Foam Medical Device in Treatment of Recurrent Aphthous Ulcers Take 10 g hydroxypropylmethyl cellulose, add 20 mL deionized water and 0.5 mL Tween 60, place in a bath at 90° C. for 30 min until complete dissolution to obtain a foam matrix, separately take 2.5 mL of a MAP solution with concentration at 10.0 mg/mL, add it into the foam matrix while stirring, and mix homogeneously to form a MAP foam medical device, wherein the MAP concentration is 1.0 mg/mL.

Gather 20 patients with minor recurrent aphthous ulcer as confirmed by experts in oral mucosa for testing. The selected patients have more than 5 ulcers with no limit on positions of the ulcers. The largest ulcer is selected as a target ulcer for observation. The target ulcer has a diameter smaller than 1 cm.

The selected patients are randomly divided into a control group and a test group. The control group is treated with the blank foam matrix that does not contain MAP, and the test group is treated with the MAP foam medical device. For both groups, the usage is 3 times per day, spraying onto the affected parts after meals, and 2 to 3 instances of spraying for each part until the affected part is completely covered by the blank foam or the MAP foam medical device. In the group sprayed with the MAP foam medical device, the pain at the affected part is significantly reduced within 5 to 10 min, the visual analogue score VAS goes from 5.0-7.0 prior to the treatment down to 1.0-2.3, and the duration of pain relief can last 3 to 10 h. For the control group, the VAS score does not change for the pain at the affected part before and after the spraying. As the use time is extended, the pain relief duration is extended, and the use interval is extended, which does not show any dependence.

After 5 days of continuous spraying, all ulcers of 7 patients in the test group are cured, and 3 patients in the control group have the ulcers cured. After 7 days of continuous spraying, all patients in the test group are cured, and 5 patients in the control group are cured (see Table 4).

TABLE 4

| Observation indexes | Control group | Test group |
| --- | --- | --- |
| Average onset time (min) | — | 6.3 ± 1.0 |
| Average VAS prior to use | 5.9 ± 1.2 | 6.0 ± 0.9 |
| Average VAS after use | 5.5 ± 1.2 | 1.1 ± 0.5 |
| Average pain relief duration (h) | — | 8.1 ± 1.8 |
| Average healing time (d) | 8.3 ± 1.9 | 3.8 ± 1.1 |

Example 20: Use of MAP Gel Drug in Treatment of Rhinitis

Take 10 g hydroxypropylmethyl cellulose, add 20 mL deionized water, place in a bath at 90° C. for 30 min until complete dissolution to obtain a gel matrix. Take a MAP solution with concentration at 2.0 mg/mL, use 0.05% citric acid to dilute by 10 times to a MAP content of 0.2 mg/mL, and obtain a MAP gel drug.

Gather 10 patients with rhinitis as confirmed by otolaryngology experts, and then have them join the groups for testing. The patients have stuffy and running noses, and the nasal discharge is viscous or mucopurulent. The MAP gel drug is administered to the patients every day in a manner of aerosol inhalation, once per day. After 3 days of using the MAP gel drug, all 10 patients have the stuffiness mitigated to various degrees. After 7 days of the use, all patients have the stuffiness mitigated, and no tested patients have mucopurulent or viscous nasal discharge. It proves that the MAP gel drug according to the present invention can be used for treatment of rhinitis.

Example 21: Use of MAP Foam Drug in Treatment of Rhinitis

Take 10 g hydroxypropylmethyl cellulose, add 20 mL deionized water and 0.5 mL Tween 60, place in a bath at 90° C. for 30 min until complete dissolution to obtain a foam matrix. Take a MAP solution with concentration at 2.0 mg/mL, use 0.05% citric acid to dilute by 10 times to a MAP content of 0.2 mg/mL, and obtain a MAP foam drug.

Gather 10 patients with rhinitis as confirmed by otolaryngology experts, and then have them join the groups for testing. The patients have stuffy and running noses, and the nasal discharge is viscous or mucopurulent. The MAP foam drug is administered to the patients every day via aerosol inhalation, once per day. After 2 days of using the MAP foam drug, all 10 patients have the stuffiness mitigated to various degrees. After 5 days of the use, all patients have the stuffiness mitigated, and no tested patients have mucopurulent or viscous nasal discharge. It proves that the MAP foam drug according to the present invention can be used for treatment of rhinitis.

Example 22: Use of MAP Foam Disinfecting Product in Treatment of Otitis Media Take a MAP solution, mix with guar gum, propanetriol and Tween 69 at a volumetric ratio of 2:1:1:0.5, add water for injection, use citric acid to adjust to pH 3.0, and prepare a MAP foam disinfecting product with the MAP content at 1.5 mg/mL.

Gather 10 patients with acute suppurative otitis media as confirmed by otolaryngology experts, and then have them join the groups for testing. The patients have earaches and pus flowing out of the ears. The patients are administered the MAP foam disinfecting product every day 3 times per day. After 1 day of using the MAP foam disinfecting product, all 10 patients no longer have the symptom of earache, and the pus in the ears is decreased. After 5 days of the use, no patients have pus flowing out of the ears. It proves that the MAP foam disinfecting product according to the present invention can be used in treatment of otitis media.

Example 23: Use of MAP Gel Medical Device in Treatment of Conjunctivitis

Take 10 g alginates, add 20 mL deionized water, place in a bath at 90° C. for 30 min until complete dissolution to obtain a gel matrix. Take a MAP solution, dilute with physiological saline, use acetic acid to adjust to pH 6.0, and obtain a MAP gel medical device, wherein the MAP concentration is 3 mg/mL.

Select 15 patients with conjunctivitis, who have manifestations of conjunctival congestion, watery secretion, and irritating sensation in eyes. They are confirmed by ophthalmologists and then join the groups for testing. Drop the MAP gel medical device above at the affected part of the eyes 4 times per day. After spraying with the MAP gel medical device, the irritating sensation is weakened at the affected part within 30 min, and the duration of weakened irritation can last for 2 to 5 h on the 1st day of the use of the device. After 5 days of continuous spraying, the irritating sensation is gone, conjunctival congestion is mitigated, and the secretion is decreased. After 7 days of continuous spraying of the MAP gel medical device above, the irritation and conjunctival congestion disappear for all patients, and the secretion becomes normal. It proves that the MAP gel medical device according to the present invention can be used for treatment of conjunctivitis.

Example 24: Use of MAP Foam Medical Device in Treatment of Conjunctivitis

Take 10 g gelatin and 1 g polyethylene glycol sodium dodecyl sulfate, add 20 mL deionized water, place in a bath at 90° C. for 30 min until complete dissolution to obtain a foam matrix. Take a MAP solution, dilute with physiological saline, use acetic acid to adjust to pH 6.0, and obtain a MAP foam medical device, wherein the MAP concentration is 3 mg/mL.

Select 15 patients with conjunctivitis, who have manifestations of conjunctival congestion, watery secretion, and irritating sensation in eyes. They are confirmed by ophthalmologists and then join the groups for testing. Drop the MAP foam medical device above at the affected part of the eyes 4 times per day. After spraying with the MAP gel medical device, the irritating sensation is weakened at the affected part within 10 min, and the duration of weakened irritation can last for 4 to 8 h on the 1st day of the use of the device. After 3 days of continuous spraying, the irritating sensation is gone, conjunctival congestion is mitigated, and the secretion is decreased. After 5 days of continuous spraying of the MAP foam medical device above, the irritation and conjunctival congestion disappear for all patients, and the secretion becomes normal. It proves that the MAP foam medical device according to the present invention can be used for treatment of conjunctivitis.

Example 25: Use of MAP Liquid Healthcare Product in Treatment of Pharyngitis Take a MAP solution, dilute with physiological saline, use acetic acid to adjust to pH 5.0, and obtain a MAP liquid healthcare product, wherein the MAP concentration is 2.0 mg/mL.

Select 16 patients with acute pharyngitis, who have manifestations of dry throat, itching, minor pain, burning sensation and foreign object sensation, and then throat pain, most of which are burning pains, and accompanied by mucosal hyperemia. They are confirmed by otolaryngologists, and then join the groups. Spray the MAP liquid healthcare product above at the affected part 3 times per day after meals. After spraying with the MAP liquid healthcare product, the pain or itching at the affected part is reduced within 14 to 20 min, and the duration of pain relief can last 2.5 to 3.0 h. After 5 days of continuous use, the feeling of pain at throat is gone, and the throat returns to normal conditions from mucosal hyperemia. It proves that the MAP liquid healthcare product according to the present invention can be used for treatment of pharyngitis.

Example 26: Use of MAP Foam Healthcare Product in Treatment of Pharyngitis

Take a MAP solution, mix with acrylamide and propanetriol at a mass ratio of 2:1:1, dilute with physiological saline, use acetic acid to adjust to pH 5.0, and obtain a MAP foam healthcare product, wherein the MAP concentration is 2.0 mg/mL.

Select 16 patients with acute pharyngitis, who have manifestations of dry throat, itching, minor pain, burning sensation and foreign object sensation, and then throat pain, most of which are burning pains, and accompanied by mucosal hyperemia. They are confirmed by otolaryngologists, and then join the groups. Spray the MAP foam healthcare product above at the affected part 3 times per day after meals. After spraying with the MAP foam healthcare product, the pain or itching at the affected part is reduced within 3 to 8 min, and the duration of pain relief can last 5 to 10.0 h. After 4 days of continuous use, the feeling of pain at throat is gone, and the throat returns to normal conditions from mucosal hyperemia. It proves that the MAP foam healthcare product according to the present invention can be used for treatment of pharyngitis.

Example 27: Use of MAP Liquid Drug in Treatment of Laryngitis

Take a MAP solution, use citric acid to adjust to pH 6.2, and obtain a MAP liquid drug, wherein the MAP concentration is 3 mg/mL.

Select 10 patients with acute laryngitis, who have manifestations of dry throat, itching, pricking sensation, burning sensation and foreign object sensation. They are confirmed by otolaryngologists, and then join the groups. Spray the MAP liquid drug above at the affected part 3 times per day after meals. After spraying with the MAP liquid drug, the itching or pain at the affected part is reduced within 7 to 30 min, and the duration of pain relief can last 1.0 to 2.0 h. After 5 days of continuous use, the feeling of pain, burning sensation and foreign object sensation at throat are all gone. It proves that the MAP drug according to the present invention can be used for treatment of laryngitis.

Example 28: Use of MAP Foam Drug in Treatment of Laryngitis

Take a MAP solution, mix with hydroxypropylmethyl cellulose, propanetriol and Tween 60 at a mass ratio of 3:2:1:0.5, use citric acid to adjust to pH 6.2, and obtain a MAP foam drug, wherein the MAP concentration is 3 mg/mL.

Select 10 patients with acute laryngitis, who have manifestations of dry throat, itching, pricking sensation, burning sensation and foreign object sensation. They are confirmed by otolaryngologists, and then join the groups. Spray the MAP foam drug above at the affected part 3 times per day after meals. After spraying with the MAP foam drug, the pain or itching at the affected part is reduced within 1 to 6 min, and the duration of pain relief can last 3.0 to 7.0 h. After 3 days of continuous use, the feeling of pain, burning sensation and foreign object sensation at throat are all gone. It proves that the MAP drug according to the present invention can be used for treatment of laryngitis.

Example 29: Use of MAP Gel Healthcare Product in Treatment of Tracheitis

Take a MAP solution, mix with methyl cellulose and propanediol at a mass ratio of 2:2:1, use acetic acid to adjust to pH 5.0, and obtain a MAP gel healthcare product, wherein the MAP concentration is 3.0 mg/mL.

Gather 12 patients with tracheitis, whose clinical manifestations include cough, expectoration, accompanied by shortness of breath. The patients must be confirmed by respiratory physicians before they can join the groups for testing. The patients are treated via aerosol inhalation, once per day and 30 min each time. After 3 days of use, the patients have mitigated cough and reduced amount of expectoration. After 7 days of use, no patients have expectoration, and 1 patient still has a slight cough. It proves that the MAP gel healthcare product according to the present invention can be used for treatment of tracheitis.

Example 30: Use of MAP Foam Healthcare Product in Treatment of Tracheitis

Take a MAP solution, mix with methyl cellulose, propanediol, and fatty alcohol at a mass ratio of 2:2:1:0.1, use acetic acid to adjust to pH 5.0, and obtain a MAP foam healthcare product, wherein the MAP concentration is 3.0 mg/mL.

Gather 12 patients with tracheitis, whose clinical manifestations include cough, expectoration, accompanied by shortness of breath. The patients must be confirmed by respiratory physicians before they can join the groups for testing. The patients are treated via aerosol inhalation, once per day and 30 min each time. After 2 days of use, the patients have mitigated cough and reduced amount of expectoration. After 5 days of use, no patients have expectoration or cough. It proves that the MAP foam healthcare product according to the present invention can be used for treatment of tracheitis.

Example 31: Use of MAP Gel Drug and Foam Drug in Treatment of Esophagitis

Take a MAP solution, mix with methyl cellulose and propanediol at a mass ratio of 2:2:1, and the pH is 5.5, wherein the MAP concentration is 2.5 mg/mL.

Take a MAP solution, mix with methyl cellulose, propanediol, and Tween 60 at a mass ratio of 2:2:1:0.2, and the pH is 5.5, wherein the MAP concentration is 2.5 mg/mL.

Gather 20 patients with esophagitis for test. According to the esophagoscopy, the patients have the following manifestations: congestion, edema, surface erosion and small and superficial ulcers of esophageal mucosa, and the patients are confirmed by doctors in digestive internal medicine and then join the groups. The patients are randomly placed in a gel drug treatment group or a foam drug treatment group, and the drug is administered to the patients via an esophagoscope, 2 times per day and 3 mL each time. For the gel drug treatment group, on the 3rd day of treatment, the scores of esophageal surface ulcer exudation and congestion both decrease from 3 in the beginning to 2 (see Table 3 for the scoring criteria). On the 6th day of treatment, the scores of esophageal surface ulcer exudation and congestion decrease to 1. On the 9th day of treatment, the scores of esophageal surface ulcer exudation and congestion decrease to 0. For the foam drug treatment group, on the 2nd day of treatment, the scores of esophageal surface ulcer exudation and congestion both decrease from 3 in the beginning to 2. On the 4th day of treatment, the scores of esophageal surface ulcer exudation and congestion decrease to 1. On the 6th day of treatment, the scores of esophageal surface ulcer exudation and congestion decrease to 0. It proves that the MAP gel drug and foam drug can both be used for treatment of esophagitis, and the foam formulation has better therapeutic effect.

Example 32: Use of MAP Liquid Drug in Treatment of Gastritis

Take a MAP solution, and use acetic acid aqueous solution to adjust to pH 4.5, wherein the MAP concentration is 2.5 mg/mL. Furthermore, wrap the MAP hydrogel drug in a gastrically soluble coating material to form a gastrically soluble sustained-release formulation.

Gather 10 patients of gastritis for testing, the patients having been diagnosed and confirmed by doctors in digestive internal medicine using gastroscopy before they join the study. The selected patients take the gastrically soluble sustained-release formulation that contains the MAP liquid drug through oral administration once per day and 1 tablet each time. After 3 days of treatment, perform gastroscopy on the subjects, and the subjects have their gastric ulcer surfaces healed to various degrees. After 5 days of treatment, perform gastroscopy on the subjects, and the subjects have all gastric ulcer surfaces healed.

Example 33: Use of MAP Foam Drug in Treatment of Gastritis

Take a MAP solution, add carboxymethyl cellulose, glycerin and Tween 20 at a volumetric ratio of 2:1:1:0.5, and obtain a MAP foam drug, wherein the MAP concentration is 2.5 mg/mL. Furthermore, wrap the MAP foam drug in a gastrically soluble coating material to form a gastrically soluble sustained-release formulation.

Gather 10 patients of gastritis for testing, the patients having been diagnosed and confirmed by doctors in digestive internal medicine using gastroscopy before they join the study. The selected patients take the gastrically soluble sustained-release formulation that contains the MAP foam drug through oral administration once per day and 1 tablet each time. After 2 days of treatment, perform gastroscopy on the subjects, and the subjects have their gastric ulcer surfaces healed to various degrees. After 4 days of treatment, perform gastroscopy on the subjects, and the subjects have all gastric ulcer surfaces healed.

Example 34: Use of MAP Gel Drug in Treatment of Acute Enteritis

Mix MAP freeze-dried powder with methyl cellulose and propanetriol at a mass ratio of 2:2:1 to prepare a MAP gel drug, wherein the MAP concentration is 1.0 mg/mL. Furthermore, wrap the MAP gel drug in an enteric coating material to form an enteric sustained-release formulation.

Gather 10 patients with acute enteritis, who have clinical manifestations of nausea, vomiting, and diarrhea, and the patients have been diagnosed and confirmed by doctors in digestive internal medicine to have acute enteritis using enteroscopy before they join the study. The selected patients are treated with the enteric sustained-release formulation that contains MAP through oral administration once per day and 1 tablet each time. After 2 days of treatment, nausea, vomiting, and diarrhea are all mitigated in the patients, proving that the MAP gel drug can be used for treatment of acute enteritis.

Example 35: Use of MAP Foam Drug in Treatment of Acute Enteritis

Mix MAP freeze-dried powder with methyl cellulose, propanetriol and Tween 60 at a mass ratio of 2:2:1:0.1 to prepare a MAP foam drug, wherein the MAP concentration is 1.0 mg/mL. Furthermore, wrap the MAP foam drug in an enteric coating material to form an enteric sustained-release formulation.

Gather 10 patients with acute enteritis, who have clinical manifestations of nausea, vomiting, and diarrhea, and the patients have been diagnosed and confirmed by doctors in digestive internal medicine to have acute enteritis using enteroscopy before they join the study. The selected patients are treated with the enteric sustained-release formulation that contains MAP through oral administration once per day and 1 tablet each time. After 1.5 days of treatment, nausea, vomiting, and diarrhea are all mitigated in the patients, proving that the MAP foam drug can be used for treatment of acute enteritis.

Example 36: Use of MAP Gel Drug in Treatment of Endometritis

Take 10 g alginates, add 20 mL deionized water, place in a bath at 90° C. for 30 min until complete dissolution to obtain a gel matrix. Take a MAP solution, add into the gel matrix, use acetic acid to adjust to pH 6.0, and obtain a MAP gel drug, wherein the MAP concentration is 3 mg/mL.

Gather 15 patients with endometritis, whose clinical manifestations include pain in the pelvic region and increased white vaginal discharge. The patients are confirmed by gynecologists to have endometritis and then join the groups for test. Perform intrauterine administration of the above MAP gel drug, and prior to the operation, first perform bimanual examination to determine the size and position of the uterus, sterilize the vulva and vagina, detect the depth of the uterine cavity, and then send a sterilized urinary catheter into the uterine cavity via the uterine neck for 0.5 cm less than the depth of uterine cavity, slowly inject the selected drug into the uterine cavity via the urinary catheter, and when the drug completely enters the uterine cavity, pull out the urinary catheter. Rest in the supine position or with hip raised for 1 to 2 h, once per day. After 10 days of use, the tested patients do not have pain in the pelvic region, and the white vaginal discharge is normal, proving that the MAP product according to the present invention can be used for treatment of endometritis.

Example 37: Use of MAP Foam Drug in Treatment of Endometritis

Take 10 g alginates, add 20 mL deionized water and 0.5 mL Tween 60, place in a bath at 90° C. for 30 min until complete dissolution to obtain a foam matrix. Take a MAP solution, add into the foam matrix, use acetic acid to adjust to pH 6.0, and obtain a MAP foam drug, wherein the MAP concentration is 3 mg/mL.

Gather 15 patients with endometritis, whose clinical manifestations include pain in the pelvic region and increased white vaginal discharge. The patients are confirmed by gynecologists to have endometritis and then join the groups for testing. Perform intrauterine administration of the above MAP foam drug, and prior to the operation, first perform bimanual examination to determine the size and position of the uterus, sterilize the vulva and vagina, detect the depth of the uterine cavity, and then send a sterilized urinary catheter into the uterine cavity via the uterine neck for 0.5 cm less than the depth of uterine cavity, slowly inject the selected drug into the uterine cavity via the urinary catheter, and when the drug liquid completely enters the uterine cavity, pull out the urinary catheter. Rest in the supine position or with hip raised for 1 to 2 h, once per day. After 7 days of use, the tested patients do not have pain in the pelvic region, and the white vaginal discharge is normal, proving that the MAP product according to the present invention can be used for treatment of endometritis.

Example 38: Use of MAP Gel Drug in Treatment of Inhalation Injuries

Take 10 g gelatin, add 20 mL deionized water, place in a bath at 90° C. for 30 min until complete dissolution to obtain a gel matrix. Take a MAP solution, add into the gel matrix, use acetic acid to adjust to pH 6.0, and obtain a MAP gel drug, wherein the MAP concentration is 5 mg/mL.

Gather 10 patients with inhalation injuries caused by inhalation of high temperature vapor, flame or dry and hot air, whose clinical manifestations include mucosal congestion, edema, erosion, exudation of cellulose, and formation of a white film. They are confirmed by otolaryngologists, and then join the groups for testing, who are treated with the above MAP gel drug. The drug is administered via aerosol inhalation, once per day and 30 min each time. At the 2nd day of treatment, the edema caused by inhalation injuries begins to subside, and the film sheds to form ulcers. At the 8th day of treatment, all patients have the ulcers healed with the average healing time at 6.0±1.8 days. It proves that the MAP gel drug according to the present invention can be used for treatment of inhalation injuries.

Example 39: Use of MAP Foam Drug in Treatment of Inhalation Injuries

Take 10 g gelatin, add 20 mL deionized water and 0.5 mL Tween 60, place in a bath at 90° C. for 30 min until complete dissolution to obtain a foam matrix. Take a MAP solution, add into the foam matrix, use acetic acid to adjust to pH 6.0, and obtain a MAP foam drug, wherein the MAP concentration is 5 mg/mL.

Gather 10 patients with inhalation injuries caused by inhalation of high temperature vapor, flame or dry and hot air, whose clinical manifestations include mucosal congestion, edema, erosion, exudation of cellulose, and formation of a white film. They are confirmed by otolaryngologists, and then join the groups for testing, who are treated with the above MAP foam drug. The drug is administered via aerosol inhalation, once per day and 30 min each time. At the 2nd day of treatment, the edema caused by inhalation injuries begins to subside, and the film sheds to form ulcers. At the 6th day of treatment, all patients have the ulcers healed with the average healing time at 3.5±1.2 days. It proves that the MAP foam drug according to the present invention can be used for treatment of inhalation injuries.

It can be seen from the above results that, MAP according to the present invention can be used, in liquid formulation, gel formulation, and foam formulation, for treatment of mucosal inflammations, and the results show that the foam formulation has better effects.

The invention claimed is:

1. A method for treating mucosal inflammation, the method comprising:
administering to a subject having mucosal inflammation an effective amount of a composition comprising a mussel adhesive protein (MAP), wherein said administering treats the mucosal inflammation, wherein the MAP comprises *M. edulis* foot protein 1 (mefp-1), wherein the MAP is present in the composition at a concentration of 0.1 to 15.0 mg/mL, wherein the composition is a medicament in the form of a gel formulation and has a pH in the range of 3.0 to 6.5, and wherein the mucosal inflammation is selected from gastritis, enterocolitis, and ulcerative colitis.

2. The method according to claim 1, wherein said administering is carried out by oral administration, sublingual administration, oral spray, or per-rectal administration.

3. The method according to claim 1, wherein the composition further comprises a gel matrix material, said gel matrix material being selected from the group consisting of cellulose derivatives, carbomer and alginates, gummi tragacanthae, gelatin, pectin, carrageenan, gellan gum, starch, xanthan gum, cationic guar gum, agar, noncellulosic polysaccharides, vinyl polymers, acrylic resins, polyvinyl alcohol, carboxyvinyl polymer, and any combination thereof.

4. The method according to claim 1, wherein the mucosal inflammation is enterocolitis.

5. The method according to claim 1, wherein the mucosal inflammation is ulcerative colitis.

6. The method according to claim 1, wherein the mucosal inflammation is gastritis.

* * * * *